US007955275B2

(12) United States Patent
Ferzli

(10) Patent No.: US 7,955,275 B2
(45) Date of Patent: Jun. 7, 2011

(54) LAPAROSCOPIC INSTRUMENT AND METHOD FOR DISTANCE MEASUREMENTS OF BODY PARTS

(76) Inventor: George S. Ferzli, Staten Island, NY (US)

( * ) Notice: Subject to any disclaimer, the term of this patent is extended or adjusted under 35 U.S.C. 154(b) by 516 days.

(21) Appl. No.: 11/895,861

(22) Filed: Aug. 28, 2007

(65) Prior Publication Data
US 2009/0062692 A1   Mar. 5, 2009

(51) Int. Cl.
*A61B 5/103* (2006.01)
*A61B 5/117* (2006.01)
(52) U.S. Cl. ........................................................ 600/587
(58) Field of Classification Search .................. 600/587, 600/564, 562; 606/207, 46, 48
See application file for complete search history.

(56) References Cited

U.S. PATENT DOCUMENTS

| 5,147,373 | A | | 9/1992 | Ferzli |
| 5,469,317 | A | * | 11/1995 | Nagata et al. .................. 235/375 |
| 5,562,102 | A | * | 10/1996 | Taylor ........................... 600/564 |
| 6,050,960 | A | | 4/2000 | Ferzli |
| 7,208,005 | B2 | * | 4/2007 | Frecker et al. ................ 606/205 |
| 7,361,172 | B2 | * | 4/2008 | Cimino ........................... 606/27 |
| 7,464,846 | B2 | * | 12/2008 | Shelton et al. ............. 227/175.1 |

* cited by examiner

*Primary Examiner* — Jeffrey G Hoekstra
(74) *Attorney, Agent, or Firm* — Jordan and Hamburg LLP

(57) ABSTRACT

A laparoscopic instrument includes an elongated barrel portion which mountably extends between operable parts for engagement with internal structures and organs of a subject patient, which are disposed at a first end of the barrel portion, and an actuating mechanism disposed at a second end of the barrel portion which remains outside the patient and which allows actuation of the instrument by the surgeon, for example by hand manipulation. The operable parts include two jaw parts which collectively define a clamp in which an opening size between the two jaw parts is selectively alterable by operation of the actuating mechanism. The operable parts further include a distance displacement sensor to effect distance measurement when the body part of the patient is received between the jaw parts and the instrument moved there along.

16 Claims, 3 Drawing Sheets

LAPAROSCOPIC INSTRUMENT AND METHOD FOR DISTANCE MEASUREMENTS OF BODY PARTS

BACKGROUND OF THE INVENTION

The present invention relates to a laparoscopic instrument useful in measuring dimensions of organs, and which is particularly well suited to facilitated collection of length data of a segment or segments of an elongated body part, including the small bowel, for example, during laparoscopic gastric bypass surgery. The invention further provides a method for obtaining such distance measurements using a laparoscopic instrument.

During laparoscopic surgery, various surgical instruments are inserted through one or more minor incisions in a patient's abdomen. A example of such a type of instrument is disclosed in U.S. Pat. No. 5,147,373 issued Sep. 15, 1992 to Ferzli, which patent is incorporated herein by reference as it pertains to the general construction of such instruments, as well as any other structural features pertinent to the practice of the invention herein.

In conjunction with the use of laparoscopic devices, a TV monitor receiving electronically converted images from an endoscope displays a view of the interior body cavity being operated on, permitting the surgeon to properly manipulate the laparoscopic instruments, as desired.

Laparoscopic surgery has made available to the patient less intrusive surgical alternatives to large incision, open surgery. Procedures heretofore requiring major invasive surgery, can now be performed laparoscopically with minimal invasion, resulting in a reduction in pain, accelerated patient recovery and significantly less scaring.

However, insofar as the surgeon performing a laparoscopic procedure generally has a view of the interior body regions of the patient accessed by the laparoscopic instruments which is limited to that shown on the aforementioned monitor, it has often been difficult for the surgeon to ascertain distances and dimensions of the various organs (or lesions) as necessary or desirable.

This drawback was addressed in U.S. Pat. No. 6,050,960 issued Apr. 18, 2000 to Ferzli, which is incorporated herein by reference. The patent disclosure describes a laparoscopic instrument in which a wheel is rotatably mounted at a distal end of an elongated barrel portion. During use, the instrument is inserted into a body cavity, through an appropriately placed incision, in accordance with conventional practice, and the internal body part to be measured is contacted by the wheel. Rotation of the wheel as it is moved in applied contact along the organ surface is converted into data representative of a distance traversed thereby.

While the aforementioned instrument is effective in the taking of measurements of dimensions and/or distances of many internal organs and the like, in many cases, such as in measurements relating to the small bowel, which is quite flexible and winding, it is difficult in practice to maintain the required continual contact of the wheel and the bowel while it is moved along a length segment thereof to be measured.

It would therefore be desirable to provide an instrument for use during laparoscopic surgery which could be inserted into a body cavity through a laparoscopic incision, and which could be used to indicate to the surgeon various internal distances and dimensions in a reliable and reproducible manner.

It would further be desirable to provide such an instrument which would be particularly useful, for example, in operations requiring organ bypass, such as in connection with intestinal or duodenum surgery, or gastric bypass, where a portion of the intestine is bypassed, ideally with a correctly sized bowel segment.

Accordingly, it is an object of the invention to provide a laparoscopic instrument which overcomes the drawbacks of the prior art.

It is a further object of the invention to provide a laparoscopic instrument which, when used during a laparoscopic procedure, permits physical measurement of various surface distances along internal body parts.

It is yet a further object of the invention to provide an instrument which structurally lends itself to material fabrication in a form permitting sterilization of the instrument in an autoclave or by means of other accepted sterilization techniques.

It is a still further object of the invention to provide a laparoscopic instrument which provides versatile measurement capabilities permitting its use independent of internal spatial considerations.

SUMMARY OF THE INVENTION

In accordance with these and other objects of the invention, there is provided a laparoscopic instrument which includes an elongated barrel portion which mountably extends between operable parts for engagement with internal structures and organs of the subject patient, which are disposed at a first end of the barrel portion, and an actuating mechanism disposed at a second end of the barrel portion which remains outside the patient and which allows actuation of the instrument by the surgeon, for example by hand manipulation.

In broad terms, the operable parts include two jaw parts which collectively define a clamp in which an opening size between the two jaw parts is selectively alterable by operation of the actuating mechanism, for example, by movement of at least one of the jaw parts to effect a change of the mutual angular relationship of the two jaw parts. In the alternative, rather than being angularly related in terms of selective relative movement, the jaw parts can be mounted via a mechanism which allows the jaw parts to remain parallel to one another during relative movement effected by operation of the actuating mechanism. To effect distance measurement, the operable parts at the first end of the barrel portion further include a distance displacement sensor. Such sensor can utilize optical or similar technologies useful and operable for sensing motion along a direction of displacement, or can simply be a rotatable measurement part contactable with the body part being measured (for example, a roller or a wheel, the respective terms being used functionally interchangeably herein), which is rotatably mounted in an orientation facing interior of the clamp opening bounded by the inner faces (i.e., confronting surfaces) of the two jaw parts and the first end of the barrel portion. During use, the organ to be measured, or a portion thereof, is positioned between the jaw parts of the clamp which have been opened sufficiently to accommodate the same therebetween. The clamp is then closed to an extent which sufficiently restrains the organ between the jaw parts, advantageously without undo trauma thereto, such that the particular distance displacement sensor is suitably positioned to take an accurate measurement as the instrument is movably displaced along the organ. For example, where a roller is used, the closure of the jaw parts about the organ permits the roller to rollably contact the organ, while undesirable movement or slippage of the organ out of the clamp from between the jaw parts comprising the same, and away from continuous contact with the roller, is concomitantly assured. Displacement of the instrument in a direction following an elongated extent of the organ, while the organ is controllably retained between the jaw parts, causes rotation of the roller (or measurement by the other selected sensing device), which in turn is converted into data representative of a distance traversed.

In accordance with an embodiment of the invention directed to a laparoscopic instrument suited to hand manipulated actuation, the actuating mechanism mounted at the second end of the barrel portion, and which is operable from outside of the patient, includes a hand grip for allowing the surgeon to reliably control movement of the instrument within the patient, and an actuating trigger which is movable, for example, about a pivotable mounting by a suitable finger motion implemented by the surgeon. The two jaw parts mounted at the first end of the barrel portion include a first jaw part mounted in fixed relationship to the longitudinal axis of barrel portion, and a second jaw part pivotably mounted for selective movement relative to the first jaw part. An actuating coupling links the second jaw part with actuating movement applied to the actuating trigger, conveniently provided in the form of a transfer rod (or multiple linked transfer rods) which extends between an extension portion of the actuating trigger connected to the transfer rod at a first end thereof and the second jaw part connected thereto at a second end thereof. Axial movement of the transfer rod imparted by movement of the actuating trigger, for example, pivoting motion, thereby serves to move (pivot) the second jaw part relative to the first jaw part to effect opening and closing of the clamp collectively comprised of the first and second jaw parts. The actuating trigger advantageously includes a finger grip for captively accommodating a finger of the surgeon, for example, the forefinger, such that movement of the finger is effective to move the trigger in either of two directions, to thereby allow control of the transfer rod in opposed directions, for respectively opening and closing the clamp. In the aforementioned embodiment, a wheel is rotatably mounted on one of the first and second jaw parts or an end of the barrel portion, advantageously the fixed first jaw part or the barrel portion for simplicity of construction in practice, positioned to rotatably contact an organ received between the two jaw parts. The wheel has a rotational axis, an orientation of which is dictated by its positioning relative to the second jaw part. For example, the wheel may be located between two ends of the first jaw, arranged to face a side of the organ contacted by the inner face of the first jaw part, in which case the rotational axis of the wheel is codirectional with the longitudinal axis of the barrel portion. Alternatively, the wheel may be located at the end of barrel portion facing longitudinally outward of the clamp opening between the two jaw parts, in which case the rotational axis will extend through the first and second jaw parts crosswise to a longitudinal axis of the first jaw part. In any event, a contact surface of the wheel protrudes into the space internally bounded collectively by the first end of the barrel portion and the first and second jaws, such that movement of the instrument along the organ reliably converts such motion into rotational motion of the wheel in a manner unimpeded by excessive frictional contact with the surface of the instrument structure to which the wheel is mounted. A suitable mechanism and/or device is provided for sensing and converting rotation of the wheel into data representative of a distance traversed over an internal body surface by the wheel in contact therewith.

A further embodiment differs with respect to the prior embodiment, in that the first jaw part, while being mounted in fixed relationship to the longitudinal axis of barrel portion as described above, includes at least a portion thereof which has a circular cross-sectional shape crosswise to the longitudinal extent thereof, and which is rotatable about a rotation axis codirectional with the longitudinal axes of the barrel portion and the first jaw part. As such, at least a portion of the surface of the first jaw part contactable with the organ to be measured received between the first and second jaw parts is rotatable, thereby itself concomitantly serving as the rotatable measurement part, and which obviates the provision of a separate wheel, as in the previous embodiment.

In yet another embodiment, the first jaw part is configured with a circular cross-section and is itself rotatable relative to the barrel portion. A transfer coupling, conveniently in the form of a rotatable shaft, is attached to the first jaw part, and extends longitudinally to the second end of the barrel portion exterior of the patient. Such configuration allows the rotational movement of the first jaw to be mechanically communicated to outside the patient in a simple manner, whereby the rotational information can be easily converted into distance measurements by suitable approaches, for example, mechanical, electronic, etc.

The above, and other objects, features and advantages of the present invention will become apparent from the following description read in conjunction with the accompanying drawings.

DETAILED DESCRIPTION OF THE PREFERRED EMBODIMENT

Figure 1:
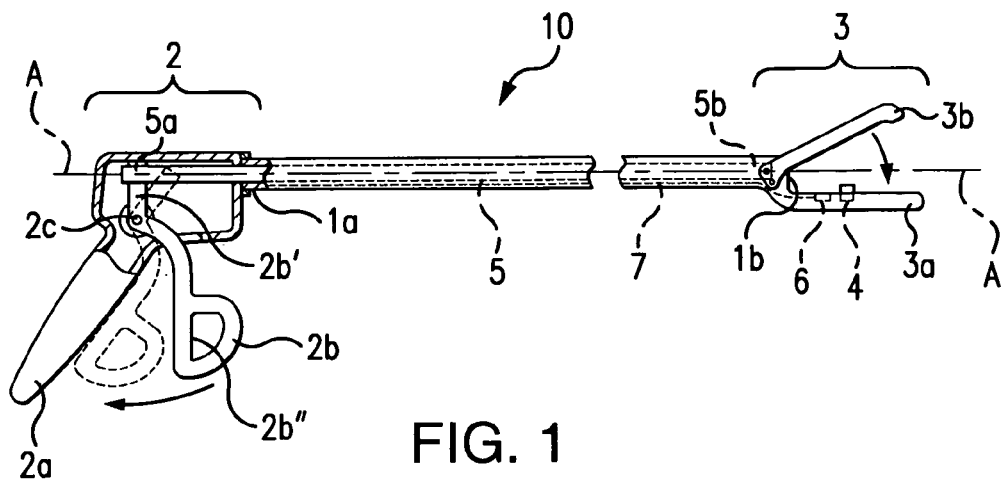
FIG. 1 is a side elevational view shown in partial cross-section of a laparoscopic instrument according to an embodiment of the invention.

Referring now to FIG. 1, an embodiment of a laparoscopic instrument in accordance with the invention is shown, generally at 10. Laparoscopic instrument 10 includes an elongated barrel portion 1 which mountably extends between operable parts 3 for engagement with internal structures and organs of the subject patient, which are disposed at a first end 1*a* of the barrel portion 1, and an actuating mechanism 2 disposed at a second end 1*b* of the barrel portion 1 which remains outside of the patient and which allows actuation of the instrument by the surgeon, for example by hand manipulation.

In broad terms, the operable parts 3 include two jaw parts 3*a* and 3*b* which collectively define a clamp in which an opening size between the two jaw parts 3*a*, 3*b* is selectively alterable by operation of the actuating mechanism 2, for example, by movement of at least one of the jaw parts 3*a*, 3*b* (in the illustrated example, specifically, jaw part 3*b*) which effects a change of the mutual angular relationship of the two jaw parts 3*a*, 3*b*. In the alternative, rather than being angularly related in terms of selective relative movement, the jaw parts can be mounted via a mechanism which allows the jaw parts 3*a*, 3*b* to remain parallel to one another during relative movement effected by operation of the actuating mechanism 2. An example of a possible mechanism for achieving this end is disclosed in U.S. Pat. No. 6,238,414 issued to Griffiths, which is incorporated herein by reference.

To effect distance measurement, the operable parts 3 at the first end 1a of the barrel portion 1 further include, in the example, a rotatable measurement part. In the depicted example of FIG. 1, such rotatable part takes the form of a roller or a wheel 4 (the respective terms being used functionally interchangeably herein), rotatably mounted in an orientation facing interior of the clamp opening bounded by the inner faces (i.e., confronting surfaces) of the two jaw parts 3a, 3b and the first end 1a of the barrel portion. During use, the organ to be measured (not shown in FIG. 1), or a portion thereof, is positioned between the jaw parts 3a, 3b of the clamp which have been opened sufficiently to accommodate the same therebetween. The clamp (comprised of jaw parts 3a, 3b) is then closed to an extent permitting the roller 4 to rollably contact the organ and also restrain, to a desired gentle degree, undesirable movement or slippage of the organ out of the clamp from between the jaw parts comprising the same, and away from continuous contact with the roller 4. Displacement of the instrument 10 in a direction following an extent of the organ, while the organ is controllably retained between the jaw parts 3a, 3b, causes rotation of the roller 4, which in turn is converted into data representative of a distance traversed. This is accomplished, for example, by provision of a rotation sensor 6 facing the roller 4 which transmits rotational data conveniently via a wire 7 which runs the length of the barrel portion 1, and out to a convertor (not shown) for conversion into distance data.

The illustrated example of FIG. 1 is directed to hand manipulated actuation. As such, the actuating mechanism 2 mounted at the second end 1b of the barrel portion 1, and which is operable from outside of the patient, includes a hand grip 2a for allowing the surgeon to reliably control movement of the instrument 10 within the patient, and an actuating trigger 2b which is movable about a mounted pivot 2c by a suitable finger motion implemented by the surgeon.

As shown in FIG. 1, the first jaw part 3a is optionally mounted in fixed relationship to a longitudinal axis A of barrel portion 1, and the second jaw part 3b is pivotably mounted for selective movement relative to the first jaw part 3a. An actuating coupling links the second jaw part 3b with actuating movement applied to the actuating trigger 2b, conveniently provided in the form of a transfer rod 5 which extends between an extension portion 2b' of the actuating trigger 2b connected to the transfer rod 5 at a first end 5a thereof and the second jaw part 3b, connected thereto at a second end 5b of the transfer rod 5. Axial movement of the transfer rod 5 imparted by pivoting movement of the actuating trigger 2b thereby serves to pivot the second jaw part 3b relative to the first jaw part 3a to effect opening and closing of the clamp collectively comprised of the first and second jaw parts 3a, 3b. The actuating trigger 2b advantageously includes a finger grip 2b" for captively accommodating a finger of the surgeon, for example, the forefinger, such that movement of the finger is effective to move the trigger 2b in either of two directions, to thereby allow control of the transfer rod 5 in two opposed directions, for respectively opening and closing the clamp by movement of the second jaw part 3b.

Figure 2:
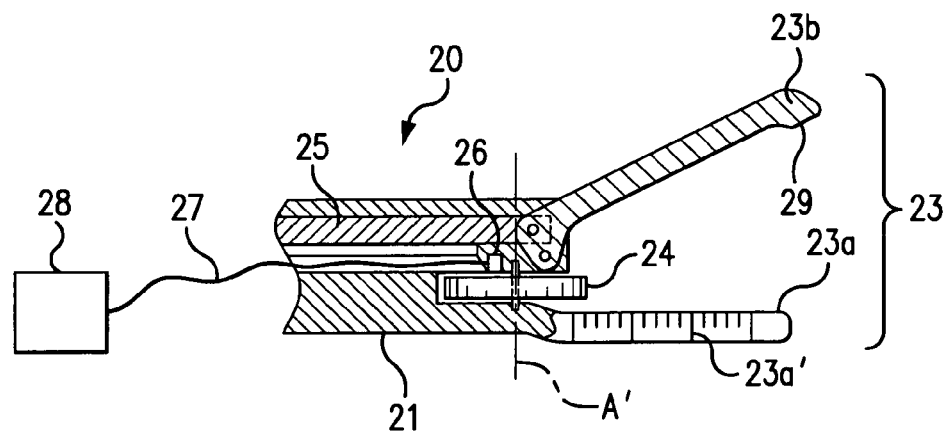
FIG. 2 is a detail cross-sectional partial view of another embodiment having an alternative wheel placement to the embodiment of FIG. 1.

Turning now to FIG. 2, an alternative embodiment of a laparoscopic instrument in accordance with the invention, generally designated by the reference numeral 20, differs from the embodiment of FIG. 1 with regard to placement of the measurement wheel, and therefore only the operable parts thereof which are inserted into the patient are depicted. Analogous with the embodiment of FIG. 1, the laparoscopic instrument includes an actuating mechanism (not shown) which remains outside of the patient and which allows actuation of the instrument by the surgeon, such mechanism being advantageously disposed at an end of a barrel portion 21, and operable parts 23 located at the other end of the barrel portion 21. As in the previously described embodiment, the operable parts 23 include two jaw parts 23a and 23b which collectively define a clamp in which an opening size between the two jaw parts 23a, 23b is selectively alterable by operation of the actuating mechanism. In the depicted example, jaw part 23b is pivotably mounded for angular movement relative to fixed jaw part 23a when movement is imparted via a transfer rod 25 from the actuating mechanism 2.

In the embodiment of FIG. 2, a wheel 24 is rotatably mounted to an end of barrel portion 21 facing longitudinally outward of the opening between the two jaw parts 23a, 23b, and having a rotational axis A' extending through the jaw parts 23a, 23b crosswise to a longitudinal axis of the fixed jaw part 23a. A contact surface of the wheel 24 protrudes into the space internally bounded collectively by the end of the barrel portion 21 and the jaw parts 23a, 23b, such that movement of the instrument along an organ reliably converts such motion into rotational motion of the wheel 24 in a manner unimpeded by excessive frictional contact with the surface of the instrument structure to which the wheel is mounted. A suitable mechanism and/or device is provided for sensing and converting rotation of the wheel into data representative of a distance traversed over an internal body surface (organ, etc.) by the wheel in contact therewith. In the depicted example, these are provided in the form of a sensor 26 connected via a wire 27 (or other suitable conductor) to a convertor 28. Convertor 28 can either be located separate of the instrument 20, or be incorporated directly therein. Optionally, at least one of the jaw parts 23a, 23b (in the depicted example, jaw part 23b can include a raised region 29 which acts concomitantly as a safety feature preventing complete closure of opening between jaw parts 23a, 23b and possible inadvertent damage to internal tissue of an organ received therebetween, and as a stop inhibiting slippage of the organ outward of the space between the jaw parts 23a, 23b. As such, if so provided, a height of the raised region 29 will be prescribed as dictated by the particular application (i.e., organ to be measured) to which it is directed. Additional, a series of ruled graduations 23a' can optionally be provided along one (or both) of the jaw parts 23a, 23b (in the depicted example jaw part 23a to allow visual determination of the local width of the organ being measured.

Figure 3:
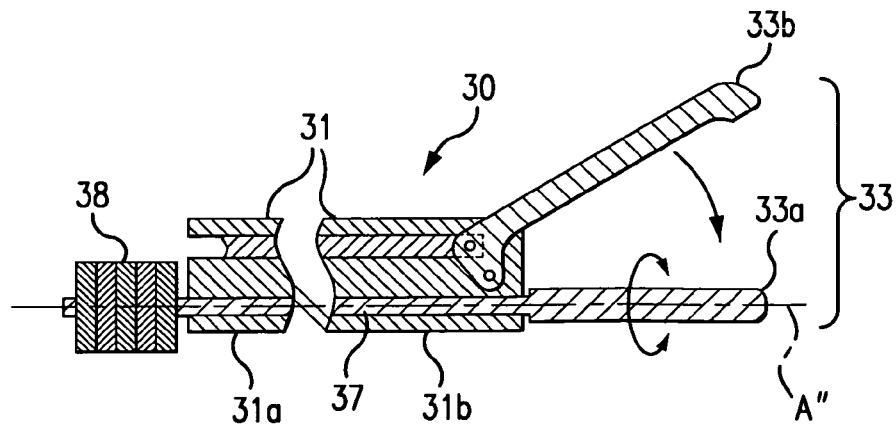
FIG. 3 is a detail cross-sectional partial view of a laparoscopic instrument according to another embodiment of the invention.

Turning now to FIG. 3, another embodiment of a laparoscopic instrument is shown, generally designated 30. As in the prior embodiments, operable parts 33 are carried at a first end 31a of the barrel portion 31, and include rotatable jaw part 33a fixed codirectionally with respect to a longitudinal barrel axis and a pivotably mounted jaw part 33b movable with respect thereto. An actuating mechanism analogous to that provided in the prior described embodiments is also provided at a second end 31b of a barrel portion 31, depiction of which is, however, omitted for clarity of illustration of other elements of the instrument 30. Rotatable jaw part 33a is rotatable about a rotation axis A", and is carried at the end of a rotatable transmission 37 (conveniently a shaft or series of connected shafts) which runs along a sufficient length of the barrel portion 31 to transmit rotation of the rotatable jaw part to outside of the patent (in the example depicted, to the second end 31b of barrel portion 31), and which concomitantly serves as a support for the rotatable jaw part 33a. A suitable device for converting rotation of the rotatable jaw part 33a in contact with an organ, and in turn rotation of the rotatable transmission 37 is provided, conveniently, for example, in the form of a simple rotary analog counter 38. A more complex or electronic device for rotational conversion into a linear representation can of course be substituted therefor, without departure from the invention.

Figure 4:
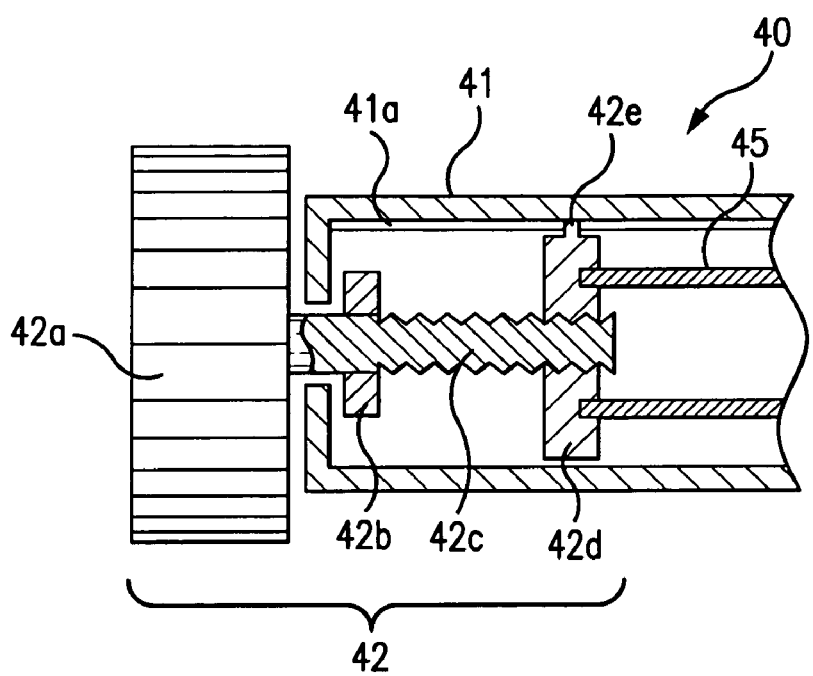
FIG. 4 is a cross-sectional detail view of another embodiment of the invention depicting an alternative actuating mechanism employing a rotatable knob which imparts linear movement to the actuating coupling.
Figure 5:
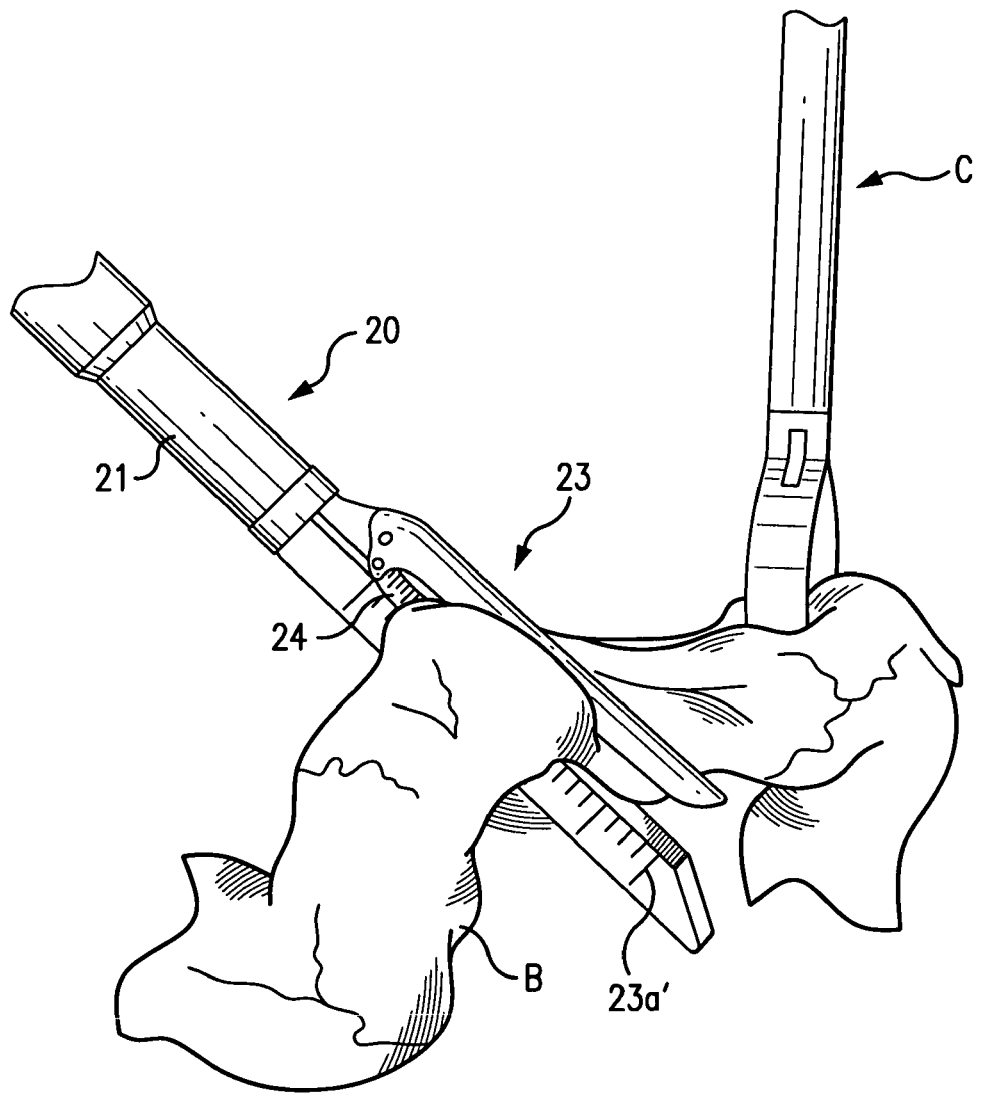
FIG. 5 is an explanatory view of a method according to the invention in which a small bowel is used as an example of an organ being measured.

FIG. 4 depicts an alternative embodiment in which the actuating mechanism 42 is rotationally operated, rather that by use of a trigger-type operation. Actuating mechanism 42 (which in the example shown is adapted to hand manipulation) includes a knob 42a captively held to a barrel portion 41, conveniently by a retainer bushing 42b sized larger than an opening in barrel portion 41 through which a threaded shaft 42c extends internally of the barrel portion 41. Threaded shaft 42c threadably engages an internally threaded advancement body 42d to which an actuating coupling 45 is attached. Advancement body 42d includes a pin 42e which extends into a key-way (groove) 41a in barrel portion 41 which acts cooperatively to prevent rotation of advancement body 42d when knob 42a is rotated.

The rotational actuating mechanism of the type depicted in FIG. 4 readily lends itself to automated operation, such as by use of a motor which can be electronically controlled to effect actuation, rather than direct hand manipulation. This is particularly advantageous and adaptive for use in, for example, robotic surgery.

A method in accordance with the invention utilizes a laparoscopic instrument according generally to the above guidelines to take distance measurements along selected body parts of a patient. The disclosed method is particularly advantageously applied in bypass surgery in which, for example, portions of the small intestine, duodenum, etc. are bypassed.

Turning to FIG. 4, in which a small bowel B is used as an example of an organ being measured by the laparoscopic instrument according to the invention, the forward end of the instrument 20, including a portion of the barrel portion 21, is inserted into a body cavity of the patient, and the organ or other body part to be measured, for example, the small bowel B in the depicted example is located forward of the jaw parts 23 of the instrument 20, conveniently assisted by controlled manipulation of a laparoscopic clamp C (conveniently of conventional design) which effectively immobilizes the bowel B to allow the instrument to be properly positioned. The clamp part of laparoscopic instrument 20 defined by the jaw parts 23 is opened by actuation of the actuating mechanism (not shown), and the instrument 20 is moved forward capturing the organ (bowel B) in the opening between the jaw parts 23. The clamp part (jaw parts 23) is then closed sufficiently to adequately restrain the organ to a desired degree, and such that the displacement measurement mechanism (wheel 24) is positioned to accurately take a distance measurement as the instrument 20 is moved laterally relative thereto. The surgeon then moves the instrument 20 along the organ (i.e., crosswise to the longitudinal axis of the barrel portion 21) while the organ is restrained within the sufficiently-reduced gap between the two jaw parts (in the orientation as depicted). An output of the displacement measurement mechanism (wheel 24) is then converted into useful data representative of actual distance traversed by the instrument 20 relative to the organ (bowel B). As mentioned above, and as can be seen in FIG. 4, ruled graduations 23a' permit visual gauging of a local width of bowel B.

It is noted that many variations on, and combination of, the above described features are contemplated. It is further recognized that many convenient features available in connection with currently available laparoscopic instruments can be particularly advantageously embodied in a commercially designed laparoscopic instrument incorporating the principles described herein. For example, the barrel portion and actuating coupling need not each be made as a single member, but rather, may be constructed as a separably joined unit made up of discrete segments which would allow detachment of a forward end containing the jaw parts (and which is inserted into the body cavity) from a rearward portion containing the actuating mechanism, to thereby allow either sterilization of the contacting portion of the device apart from the non-contacting portion remaining outside of the body, or disposability of the portion containing the jaw parts after biological contamination thereof. Such feature is also particularly advantageous insofar as different size jaw parts can be made available, for replacement to the actuating mechanism portion as needed for a particular medical application.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A laparoscopic instrument for distance measurement of an elongated dimension of an internal body part of a patient, comprising:
    an elongated barrel portion;
    first and second jaw parts being carried at a first end of said barrel portion and extending from said first end codirectionally with a jaw axis, at least one of said jaw parts being movable with respect to said barrel portion to effect an increase and decrease of a jaw space between said first and second jaw parts;
    an actuating mechanism carried at a position along the barrel portion spaced apart from said first end for controlling movement of said at least one of said jaw parts by movement thereof; and
    a distance displacement sensor being disposed at said first end of said barrel portion, said distance displacement sensor being configured so as to be operable for sensing a distance of displacement of the first and second jaw parts along at least a length portion of the internal body part when a portion of the body part being measured is at least partially received in said jaw space and the instrument moved so as to effect travel of the first and second jaw parts in a direction crosswise to said jaw axis along said at least a length portion of the internal body part.

2. A laparoscopic instrument according to claim 1, further comprising an actuating coupling extending between said actuating mechanism and said at least one of said jaw parts, said movement of said actuating mechanism being converted into axial displacement of said actuating coupling, said axial displacement being converted into controlled movement of said at least one of said jaw parts effecting the increase and decrease of said jaw space.

3. A laparoscopic instrument according to claim 2, wherein said actuating mechanism includes a hand grip and an actuating trigger pivotably movable relative to said hand grip for converting pivotable movement thereof into said axial displacement of the actuating coupling.

4. A laparoscopic instrument according to claim 2, wherein said actuating mechanism includes a rotatable knob linked with said actuating coupling in a manner in which rotation thereof is converted into said axial displacement of the actuating coupling.

5. A laparoscopic instrument according to claim 1, wherein said distance displacement sensor includes a rotatable part which is rollably contactable with the body part and positioned such that said rotatable part is made to rotate in response to movement of the instrument along the body part when the body part is at least partially received in said jaw space.

6. A laparoscopic instrument according to claim 5, wherein said rotatable part is rotatably mounted in an orientation facing interior of a clamp opening bounded by inner confronting surfaces of the first and second jaw parts and the first end of the barrel portion.

7. A laparoscopic instrument according to claim 6, wherein said rotatable part is located between two ends of the first jaw, arranged to face a side of the body part contacted by the inner confronting surface of the first jaw part, a rotational axis of the rotatable part being codirectional with a longitudinal axis of the barrel portion.

8. A laparoscopic instrument according to claim 6, wherein said rotatable part is located at the first end of the barrel portion facing longitudinally outward of the clamp opening between the first and second jaw parts, a rotational axis of the rotatable part extending through the first and second jaw parts crosswise to a longitudinal axis of the first jaw part.

9. A laparoscopic instrument according to claim 5, wherein one of the first and second jaw parts is mounted in fixed relationship to the barrel portion in a longitudinal direction of said barrel portion, at least a portion of said first and second jaw parts presenting a generally circular cross-sectional shape crosswise to a longitudinal extent of the one of the jaw parts and which is rotatable about a rotation axis codirectional with a longitudinal axis of the barrel portion and a corresponding longitudinal axis of each of the first and second jaw parts, said at least a portion thereby serving as the rotatable part.

10. A laparoscopic instrument according to claim 5, further comprising a rotatable transmission which runs along a length portion of the barrel portion so as to transmit a rotation of the rotatable part to outside of the patient.

11. A laparoscopic instrument according to claim 10, further comprising a device for converting rotation of the rotatable transmission into a linear measurement.

12. A laparoscopic instrument according to claim 11, wherein said device includes a rotary analog counter.

13. A laparoscopic instrument according to claim 11, wherein said device includes an electronic device for rotational conversion of said rotation of the rotatable transmission into said linear measurement.

14. A laparoscopic instrument according to claim 5, wherein one of the first and second jaw parts is configured with a generally circular cross-section and is rotatable relative to the barrel portion, thereby serving as the rotatable part.

15. A laparoscopic instrument according to claim 1, wherein a series of ruled graduations is provided along at least one of the first and second jaw parts in a position thereon allowing visual determination of a local width of the body part being measured and received in said jaw space.

16. A method of measuring an elongated dimension of an internal body part of a patient, comprising:
   inserting a forward end of a laparoscopic instrument including a barrel portion and a clamp presenting an adjustable clamp opening at a forward end of said barrel portion into a body cavity of the patient, the clamp extending forward of said barrel portion codirectionally with a clamp axis;
   opening the clamp by actuation of an actuating mechanism carried at a rearward end of the barrel portion;
   capturing at least a portion of the internal body part in the clamp opening;
   closing said clamp to reduce the clamp opening so as to adequately restrain the internal body part;
   moving the clamp crosswise to said clamp axis along at least a length portion of the internal body part; and
   sensing a distance of displacement of the clamp along said at least a length portion of the internal body part during said moving the clamp crosswise to said clamp axis.

* * * * *